(12) United States Patent
Yoshida et al.

(10) Patent No.: US 11,109,827 B2
(45) Date of Patent: Sep. 7, 2021

(54) X-RAY IMAGING APPARATUS

(71) Applicant: Shimadzu Corporation, Kyoto (JP)

(72) Inventors: Koki Yoshida, Kyoto (JP); Hidetaka Takezawa, Kyoto (JP); Shohei Okubo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/706,129

(22) Filed: Dec. 6, 2019

(65) Prior Publication Data
US 2020/0305813 A1 Oct. 1, 2020

(30) Foreign Application Priority Data
Mar. 25, 2019 (JP) .............................. JP2019-057268

(51) Int. Cl.
*A61B 6/00* (2006.01)
*A61B 6/04* (2006.01)

(52) U.S. Cl.
CPC ............ *A61B 6/463* (2013.01); *A61B 6/0407* (2013.01); *A61B 6/0487* (2020.08); *A61B 6/40* (2013.01); *A61B 6/54* (2013.01); *A61B 6/589* (2013.01)

(58) Field of Classification Search
CPC ..... A61B 6/463; A61B 6/0487; A61B 6/0407; A61B 6/40; A61B 6/54; A61B 6/589
See application file for complete search history.

(56) References Cited

U.S. PATENT DOCUMENTS

| | | | |
|---|---|---|---|
| 2012/0250973 A1* | 10/2012 | Nambu | A61B 6/12 382/132 |
| 2017/0164921 A1 | 6/2017 | Hirose et al. | |
| 2018/0214103 A1 | 8/2018 | Okubo | |
| 2019/0320995 A1* | 10/2019 | Amiri | A61B 6/463 |

FOREIGN PATENT DOCUMENTS

| | | |
|---|---|---|
| JP | 2017-104538 A | 6/2017 |
| JP | 2018-121745 A | 8/2018 |

* cited by examiner

*Primary Examiner* — Hugh Maupin
(74) *Attorney, Agent, or Firm* — Muir Patent Law, PLLC

(57) ABSTRACT

An X-ray imaging apparatus includes a table, an imager configured to capture a plurality of X-ray images, a rotating mechanism, a moving mechanism, and an image processor. The image processor is configured to generate a long image by performing processing of varying magnifications of the plurality of X-ray images based on an amount of relative movement of the table and the imager and splicing the plurality of X-ray images when imaging is performed at a plurality of imaging positions in a state in which an optical axis of X-rays radiated from an X-ray irradiator is inclined with respect to the table.

9 Claims, 8 Drawing Sheets

FIRST EMBODIMENT

FIRST EMBODIMENT

FIRST EMBODIMENT

FIRST EMBODIMENT

LONG IMAGE GENERATION

FIRST EMBODIMENT

FIRST EMBODIMENT

FIRST EMBODIMENT

COMPARATIVE EXAMPLE

SECOND EMBODIMENT

SECOND EMBODIMENT

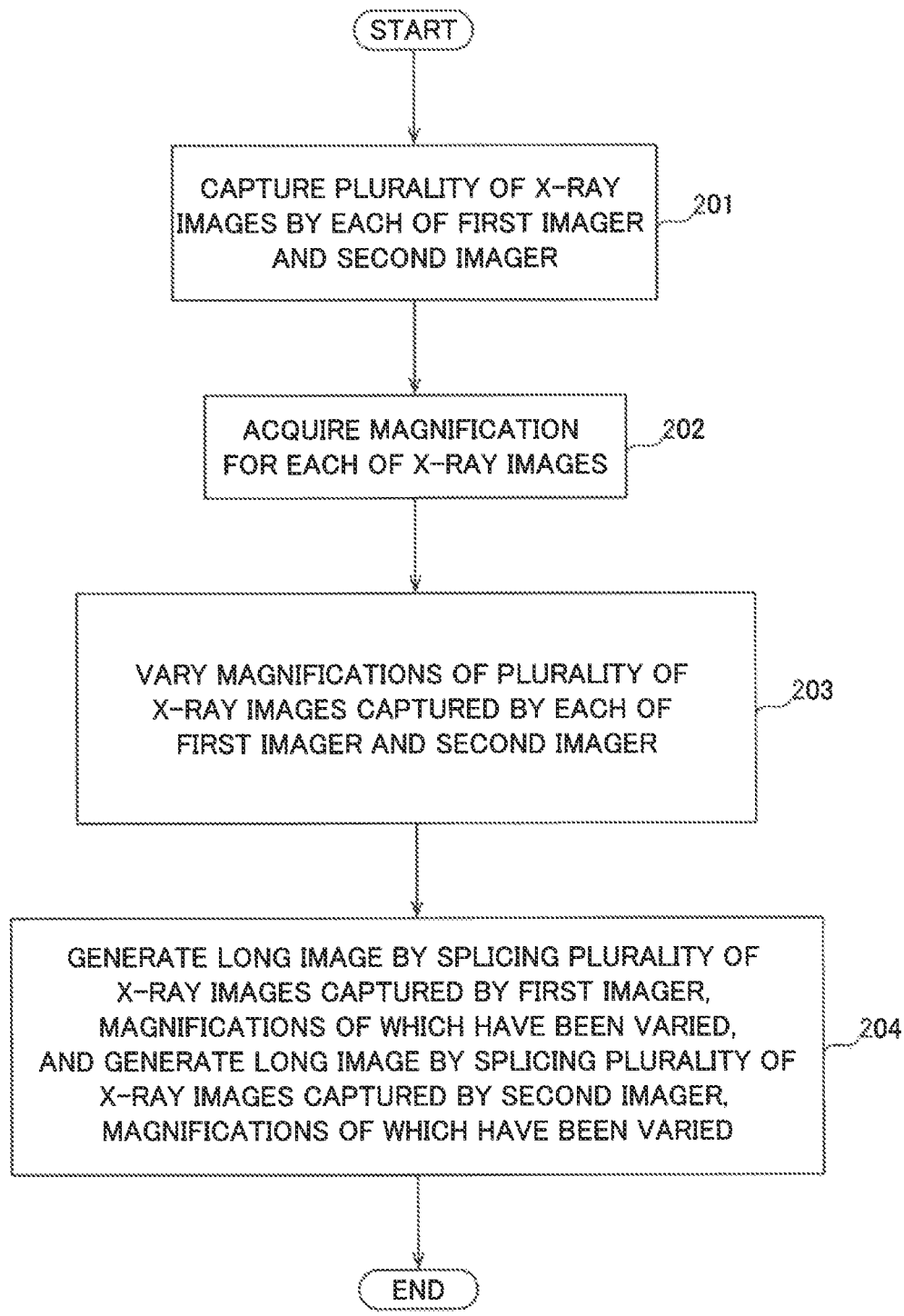

X-RAY IMAGING APPARATUS

CROSS-REFERENCE TO RELATED APPLICATIONS

This application claims the benefit of priority to Japanese Patent Application No. 2019-57268 filed on Mar. 25, 2019. The entire contents of this application are hereby incorporated herein by reference.

BACKGROUND OF THE INVENTION

Field of the Invention

The present invention relates to an X-ray imaging apparatus, and more particularly, it relates to an X-ray imaging apparatus that generates a long image by joining images captured at a plurality of imaging positions.

Description of the Background Art

Conventionally, an X-ray imaging apparatus that generates a long image by joining images captured at a plurality of imaging positions is known. Such an X-ray imaging apparatus is disclosed in Japanese Patent Laid-Open No. 2018-121745, for example.

Japanese Patent Laid-Open No. 2018-121745 discloses an X-ray imaging apparatus including a table on which a subject is placed, an imager that irradiates the subject with X-rays and detects the X-rays transmitted through the subject to capture a plurality of X-ray images, a moving mechanism that can change the relative position of the table to the imager, and an image processor that generates a long image, which is longer than each of the plurality of X-ray images, by performing processing of splicing the plurality of X-ray images. Furthermore, in the X-ray imaging apparatus disclosed in Japanese Patent Laid-Open No. 2018-121745, the moving mechanism is controlled so as to relatively move the table such that the imager is moved in the longitudinal direction of the subject. During the movement, the subject is sequentially irradiated with X-rays. Each time, the transmitted X-rays through the subject are detected to capture a fluoroscopic X-ray image. Incidentally, "X-ray fluoroscopy" is an imaging method in which the X-ray dose is relatively reduced as compared with "X-ray imaging", and is temporarily used (not saved).

The X-ray imaging apparatus disclosed in Japanese Patent Laid-Open No. 2018-121745 can generate an image (long image) longer than a single X-ray image by performing the processing of splicing X-ray images acquired by relatively moving the table and capturing images based on positional information at the time of capturing the respective X-ray images. Such a long image is particularly used for surgery, for example, which requires a large movement of an imaging range because a region to be imaged does not fit in a single X-ray image as in the case in which a contrast agent is administered to check a stenotic portion or bifurcation of a blood vessel in the lower limb, for example.

As shown in FIG. 1 of Japanese Patent Laid-Open No. 2018-121745, the case in which imaging is performed with the imager disposed in such a manner that the optical axis of the X-rays is in a vertical direction is considered. When imaging is performed with the imager disposed in such a manner that the optical axis of the X-rays is in the vertical direction, the visibility of a region of interest may decrease depending on a region to be imaged of the subject. For example, when a portion of a blood vessel to be checked, which overlaps a bone or another blood vessel in the vertical direction, is imaged in the case of imaging a blood vessel in the lower limb, X-ray irradiation in the vertical direction may result in a decrease in the visibility of the blood vessel to be checked. Therefore, imaging is performed in a state in which the imager is inclined such that the visibility of the blood vessel to be checked in the long image can conceivably be improved. However, the X-ray imaging apparatus disclosed in Japanese Patent Laid-Open No. 2018-121745 has a configuration in which the long image is generated by splicing the plurality of X-ray images captured while the imager is moved. Therefore, when a long image is generated by splicing a plurality of X-ray images captured with an imager inclined as in the case of the X-ray imaging apparatus disclosed in Japanese Patent Laid-Open No. 2018-121745, the path length of an X-ray, which has been transmitted through a subject, to an X-ray detector differs depending on a location in an X-ray image, and thus there is a disadvantage that X-ray images are not appropriately spliced at seams of the X-ray images. Therefore, an X-ray imaging apparatus is desired which can generate a long image in which a plurality of X-ray images are appropriately spliced even when the long image is generated by splicing the plurality of X-ray images captured with an imager inclined while an imaging position is changed.

SUMMARY OF THE INVENTION

The present invention is intended to solve the above problem. The present invention aims to provide an X-ray imaging apparatus capable of generating a long image in which a plurality of X-ray images are appropriately spliced even when the long image is generated by splicing the plurality of X-ray images captured with an imager inclined while an imaging position is changed.

In order to attain the aforementioned object, an X-ray imaging apparatus according to an aspect of the present invention includes a table on which a subject is placed, an imager including an X-ray irradiator configured to irradiate the subject with X-rays and an X-ray detector configured to detect the X-rays radiated from the X-ray irradiator and transmitted through the subject, the imager being configured to capture a plurality of X-ray images, a rotating mechanism configured to rotate the imager, a moving mechanism configured to move so as to change a relative position of the table to the imager, and an image processor configured to generate a long image, which is longer than each of the plurality of X-ray images, by performing processing of varying magnifications of the plurality of X-ray images based on an amount of relative movement of the table and the imager and splicing the plurality of X-ray images when imaging is performed at a plurality of imaging positions while the table and the imager are moved relative to each other in at least one of a short-side direction or a longitudinal direction of the table in a state in which the imager is rotated such that an optical axis of the X-rays radiated from the X-ray irradiator is inclined with respect to the table.

As described above, the X-ray imaging apparatus according to this aspect of the present invention includes the image processor configured to generate the long image by performing the processing of varying the magnifications of the plurality of X-ray images based on the amount of relative movement of the table and the imager and splicing the plurality of X-ray images. When imaging is performed with the imager inclined, an X-ray is incident on the table in an oblique direction. Therefore, the path length of the X-ray, which has been transmitted through the subject, to the X-ray detector differs depending on a location in the X-ray images. Therefore, as compared with the case in which imaging is performed without inclining the imager, regions having different sizes are generated in the X-ray images. In addition, the path length of the X-ray, which has been transmitted through the subject, to the X-ray detector differs depending on a location in the X-ray images, and thus the magnification of the same region of the subject varies between the X-ray images when imaging is performed while at least one of the table or the imager is moved in a state in which the imager is inclined. Thus, when the X-ray images are spliced, steps are generated at seams of the X-ray images. Therefore, with the above configuration, the processing of varying the magnifications of the plurality of X-ray images based on the amount of relative movement of the table and the imager and splicing the plurality of X-ray images is performed, and thus it becomes possible to match the magnifications of the subject that appears at the seams between the X-ray images, and the X-ray images can be appropriately spliced. Consequently, even when the long image is generated by splicing the plurality of X-ray images captured while changing the imaging position in a state in which the imager is inclined, the long image in which the X-ray images are appropriately spliced can be generated. Note that the term "magnification" refers to a ratio indicating whether the size of a region of interest of the subject that appears in the X-ray images is larger or smaller than the size of the region of interest of the subject that appears in the X-ray images when the imager is not inclined.

In the aforementioned X-ray imaging apparatus according to this aspect, the image processor is preferably configured to perform processing of varying the magnifications of the plurality of X-ray images based on at least one of an angle defined by the optical axis of the X-rays radiated from the X-ray irradiator and the longitudinal direction of the table or an angle defined by the optical axis of the X-rays radiated from the X-ray irradiator and the short-side direction of the table, both of which are formed when the optical axis of the X-rays radiated from the X-ray irradiator is inclined with respect to the table, and the amount of relative movement of the table and the imager, and splicing the plurality of X-ray images. The angle defined by the optical axis of the X-rays radiated from the X-ray irradiator and the longitudinal direction of the table, and the angle defined by the optical axis of the X-rays radiated from the X-ray irradiator and the short-side direction of the table are known values at the time of starting imaging. Therefore, with the above configuration, the magnification of each of the X-ray images can be easily varied by acquiring the amount of relative movement of the table and the imager.

In this case, the image processor is preferably configured to perform processing of varying the magnifications of the plurality of X-ray images based on the amount of relative movement of the table and splicing the plurality of X-ray images when imaging is performed while the table is moved in the longitudinal direction of the table in a state in which the optical axis of the X-rays radiated from the X-ray irradiator is inclined with respect to the longitudinal direction of the table, and when imaging is performed while the table is moved in the short-side direction of the table in a state in which the optical axis of the X-rays radiated from the X-ray irradiator is inclined with respect to the short-side direction of the table. When the table is moved in a state in which the optical axis of the X-rays is inclined with respect to the table, the magnification may vary between the X-ray images depending on the inclination direction of the optical axis of the X-rays and the moving direction of the table. That is, when the table is moved in the longitudinal direction of the table in a state in which the optical axis of the X-rays is inclined with respect to the longitudinal direction of the table, and when the table is moved in the short-side direction of the table in a state in which the optical axis of the X-rays is inclined with respect to the short-side direction of the table, the magnification varies between the X-ray images.

Accordingly, with the above configuration, even when the magnifications of the plurality of X-ray images are different from each other, the X-ray images can be appropriately spliced. Consequently, imaging is performed while the table is relatively moved in a state in which the imager is inclined such that even when the magnifications of the X-ray images are different from each other, an appropriate long image can be generated. Note that the angle defined by the optical axis of the X-rays and the longitudinal direction of the table and the angle defined by the optical axis of the X-rays and the short-side direction of the table are angles excluding 0 degrees, 90 degrees, and 180 degrees in an angle range of 0 degrees to 180 degrees.

In the aforementioned X-ray imaging apparatus according to this aspect, the image processor is preferably configured to vary the magnifications of the plurality of X-ray images such that a distance between an imaging plane parallel to a detection surface of the X-ray detector and a height position of a region of interest of the subject is the same between the plurality of X-ray images. Accordingly, with a distance between the imaging plane of any of the plurality of X-ray images and the height position of the region of interest of the subject as a reference, distances between the imaging planes of the other X-ray images and the height position of the region of interest of the subject can be the same as the reference distance. Consequently, the X-ray images can be appropriately spliced using any of the plurality of X-ray images as a reference.

In this case, the image processor is preferably configured to acquire a magnification for each of the plurality of X-ray images based on the distance between the imaging plane and the height position of the region of interest of the subject that occurs due to imaging with the imager rotated to be inclined with respect to the table, and to generate the long image while varying the magnifications of the plurality of X-ray images based on a variation in the distance between the imaging plane and the height position of the region of interest of the subject that occurs due to the relative movement of the table and the imager in at least one of the short-side direction or the longitudinal direction of the table in a state in which the imager is rotated to be inclined with respect to the table. Accordingly, distances between the imaging planes of the plurality of X-ray images and the height position of the region of interest of the subject are compared with each other such that a difference between the magnifications of the X-ray images can be easily acquired. Consequently, the magnification of each of the X-ray images can be easily varied, and the long image in which the X-ray images are appropriately spliced can be easily acquired.

The aforementioned configuration in which the magnifications of the plurality of X-ray images are varied such that the distance between the imaging plane and the height position of the region of interest of the subject is the same between the X-ray images preferably further includes a rotation angle acquirer configured to acquire a rotation angle of the imager and a position information acquirer configured to acquire position information of the table, and the image processor is preferably configured to acquire the distance between the imaging plane and the height position of the region of interest of the subject based on a moving distance of the table at each of the plurality of imaging positions and the rotation angle of the imager. The rotation angle of the imager and the height position of the region of interest of the subject are values set in advance when imaging is performed, and thus the same are known values. Therefore, with the above configuration, the moving distance of the table at each of the plurality of imaging positions is acquired such that the distance between the imaging plane and the height position of the region of interest of the subject can be easily acquired.

In the aforementioned configuration in which the magnifications of the plurality of X-ray images are varied such that the distance between the imaging plane and the height position of the region of interest of the subject is the same between the X-ray images, the height position of the region of interest of the subject is preferably settable, and the image processor is preferably configured to acquire the magnification for each of the plurality of X-ray images based on the distance between the imaging plane and the height position of the region of interest of the subject that has been set. Accordingly, even when the height position of the region of interest of the subject is changed, the magnification of each of the X-ray images can be acquired based on the changed height position of the region of interest of the subject. Consequently, it is possible to generate the long image at the height position of the region of interest that a user desires to check, and thus convenience for the user can be improved.

In the aforementioned X-ray imaging apparatus according to this aspect, the imager preferably includes a first imager and a second imager configured to capture the plurality of X-ray images in a state in which the second imager is inclined at an angle different from that of the first imager with respect to the subject, the rotating mechanism preferably includes a first rotating mechanism configured to rotate the first imager, and a second rotating mechanism configured to rotate the second imager, and the image processor is preferably configured to generate the long image by performing processing of varying the magnifications of the plurality of X-ray images captured by the first imager and splicing the plurality of X-ray images, and to generate the long image by performing processing of varying the magnifications of the plurality of X-ray images captured by the second imager and splicing the plurality of X-ray images. Accordingly, long images captured from the angles different from each other can be acquired by the first imager and the second imager with a single administration of a contrast agent. Consequently, it is possible to significantly reduce or prevent an increase in the number of administrations of the contrast agent as compared with the configuration in which the contrast agent is administered a plurality of times and one imager captures images while changing the imaging angles. Furthermore, the imaging time can be reduced, and thus the amount of radiation exposure can be decreased.

In the aforementioned X-ray imaging apparatus according to this aspect, the plurality of X-ray images and the long image preferably include images obtained by imaging a lower limb of the subject. The long image is generally generated when the lower limb of the subject is radiographed, and thus it is particularly effective to apply the present invention to an X-ray imaging apparatus that images a blood vessel of the lower limb with an imager inclined with respect to a table.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 12 is a flowchart for illustrating long image generation processing in the X-ray imaging apparatus according to the second embodiment.

DESCRIPTION OF THE PREFERRED EMBODIMENTS

Embodiments of the present invention are hereinafter described with reference to the drawings.

First Embodiment

The configuration of an X-ray imaging apparatus 100 according to a first embodiment is now described with reference to FIGS. 1 to 7.

(Configuration of X-Ray Imaging Apparatus)

Figure 1:
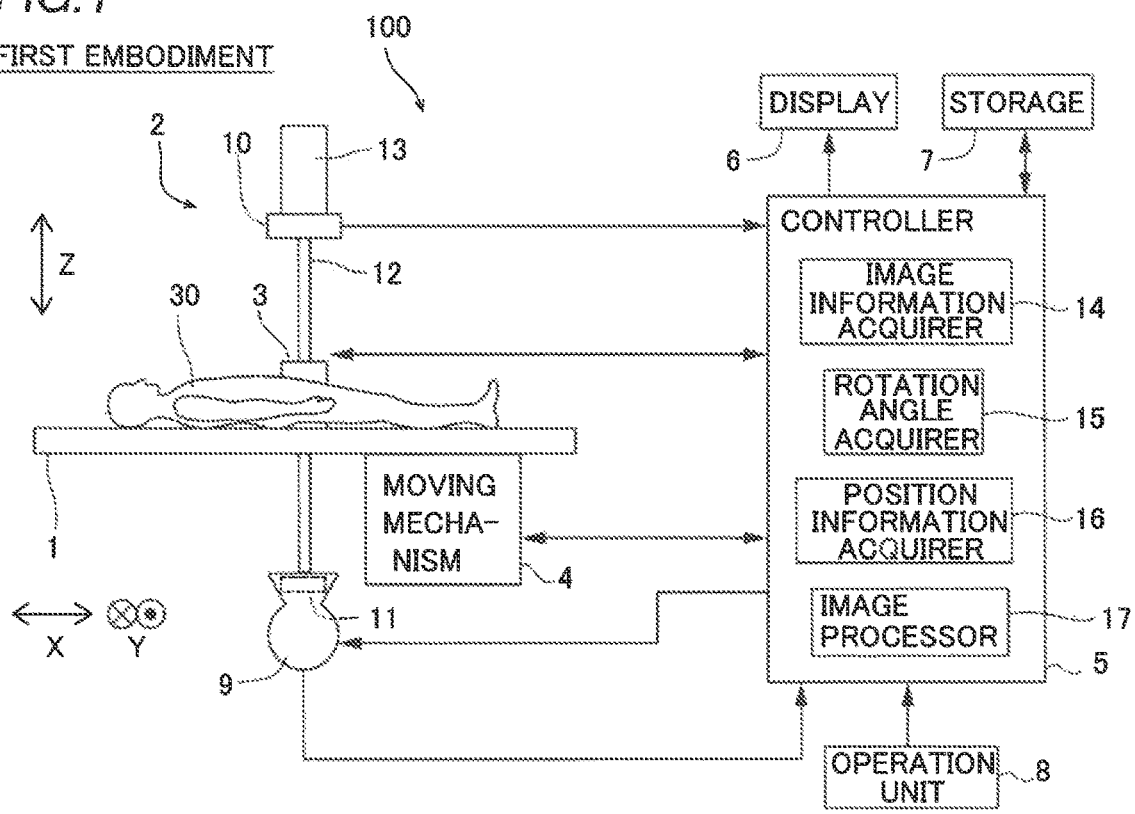
FIG. 1 is a schematic view showing the overall configuration of an X-ray imaging apparatus according to a first embodiment.

As shown in FIG. 1, the X-ray imaging apparatus 100 according to the first embodiment includes a table 1, an imager 2, a rotating mechanism 3, a moving mechanism 4, a controller 5, a display 6, a storage 7, and an operation unit 8.

A subject 30 is placed on the table 1. The table 1 has a rectangular flat plate shape in a plan view. The subject 30 is placed on the table 1 in such a manner that the head-foot direction of the subject 30 is along the long side of the rectangular shape, and the left-right direction of the subject 30 is along the short side of the rectangular shape. In this specification, the long-side direction of the rectangular shape is taken as an X direction, the short-side direction of the rectangular shape is taken as a Y direction, and a direction orthogonal to the X direction and the Y direction is taken as a Z direction. The direction (X direction) along the long side of the rectangular shape is an example of a "longitudinal direction of the table" in the claims. The direction (Y direction) along the short side of the rectangular shape is an example of a "short-side direction of the table"

in the claims. The head-foot direction of the subject 30 refers to a direction along a straight line that connects the head and the foot of the subject 30.

Figure 11:
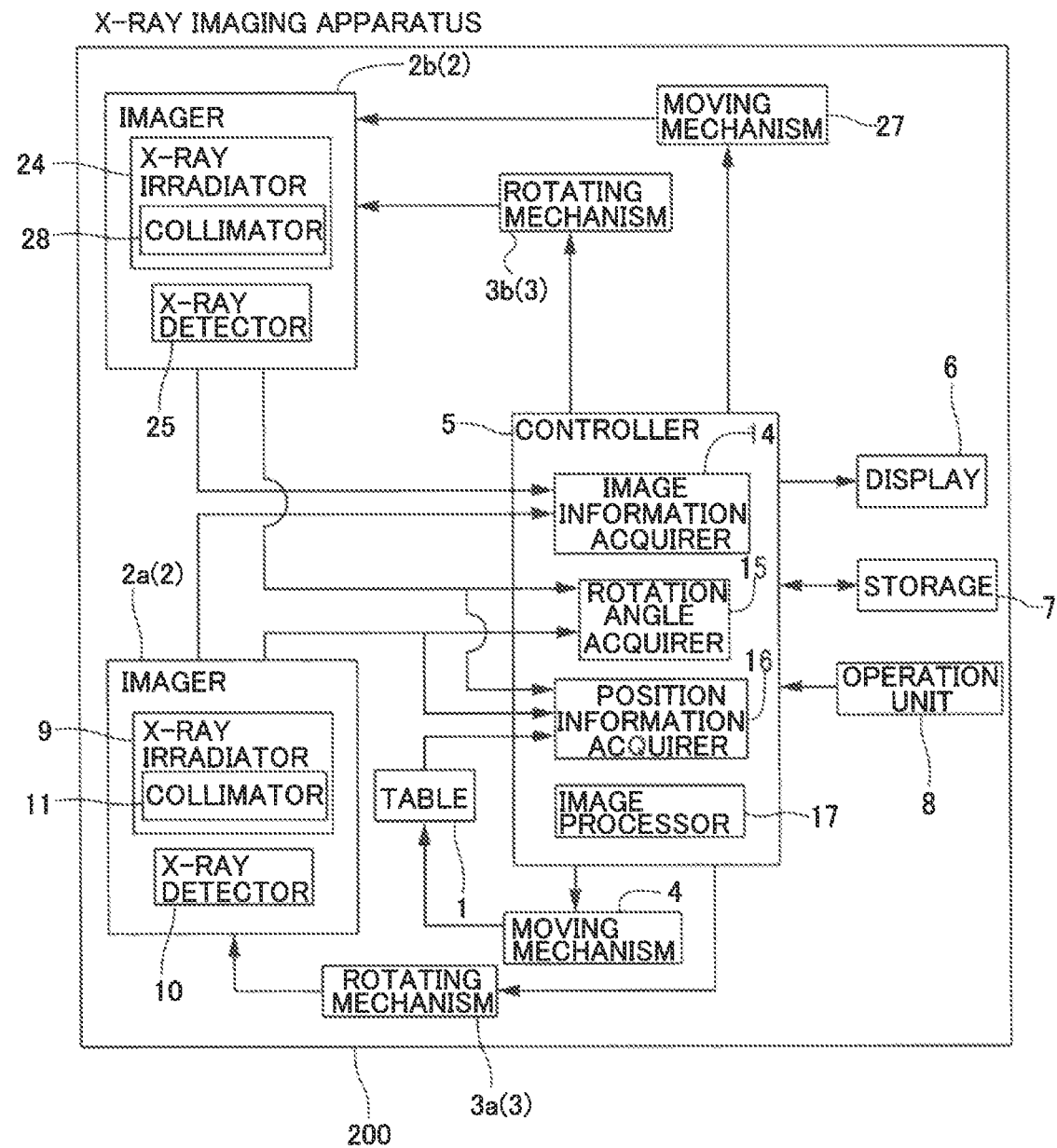
FIG. 11 is a block diagram showing the overall configuration of the X-ray imaging apparatus according to the second embodiment.

The imager 2 includes an X-ray irradiator 9 and an X-ray detector 10. The imager 2 is configured to capture X-ray images 40 (see FIG. 4). The X-ray irradiator 9 includes an X-ray source and is disposed on a first side in the Z direction with respect to the table 1. The X-ray irradiator 9 is configured to irradiate the subject 30 with X-rays when a voltage is applied thereto by an X-ray tube drive (not shown). The X-ray irradiator 9 includes a collimator 11 that can adjust an X-ray irradiation field, which is an X-ray irradiation range. Moreover, the X-ray irradiator 9 is attached to the tip of a first side of a C-shaped arm 12, as shown in FIG. 11.

The X-ray detector 10 is configured to detect X-rays radiated from the X-ray irradiator 9 and transmitted through the subject 30. The X-ray detector 10 includes a flat panel detector (FPD), for example. The X-ray detector 10 is attached to the tip of a second side (the side opposite to the X-ray irradiator 9) of the arm 12. Moreover, tips of the arm 12 are disposed in such a manner as to interpose the table 1. That is, the X-ray detector 10 is disposed on a second side (the side opposite to the X-ray irradiator 9) in the Z direction with respect to the table 1. Thus, in the X-ray imaging apparatus 100, in a state in which the subject 30 is placed on the table 1, the X-ray irradiator 9 irradiates the subject 30 with X-rays, and the X-ray detector 10 detects the X-rays transmitted through the subject 30 such that the X-ray images 40 can be captured. Furthermore, the X-ray detector 10 can be slid in a direction (the Z direction in FIG. 1) in which a slider 13 extends by the slider 13 attached to the tip of the arm 12.

The rotating mechanism 3 is configured to be able to rotate the imager 2 by rotating the arm 12 under control of the controller 5. The rotating mechanism 3 includes a moving mechanism that moves the C-shaped arm 12 along the outer periphery of the arm 12. The rotating mechanism 3 is configured to be able to rotate the arm 12 around an axis in the longitudinal direction of the table 1 and around an axis in the short-side direction of the table 1. The rotating mechanism 3 includes a motor, for example.

The moving mechanism 4 is configured to move so as to change the relative position of the table 1 to the imager 2 under control of the controller 5. Specifically, the moving mechanism 4 is configured to be able to change the relative position of the table 1 to the imager 2 by moving the table 1 in any of the X direction, the Y direction, and the Z direction. The moving mechanism 4 includes a linear movement mechanism movable in the X direction, a linear movement mechanism movable in the Y direction, and a linear movement mechanism movable in the Z direction. Each of the linear movement mechanisms includes a ball screw or a linear motor, for example.

The controller 5 is configured or programmed to control the rotating mechanism 3 to rotate the imager 2. The controller 5 is also configured or programmed to control the moving mechanism 4 to move the table 1 and the imager 2 relative to each other. The controller 5 is a computer including a central processing unit (CPU), a read-only memory (ROM), a random access memory (RAM), etc. The controller 5 includes an image information acquirer 14, a rotation angle acquirer 15, a position information acquirer 16, and an image processor 17. The controller 5 is configured or programmed to function as the image information acquirer 14, the rotation angle acquirer 15, and a position information acquirer 16 by executing various programs stored in the storage 7.

Figure 2:
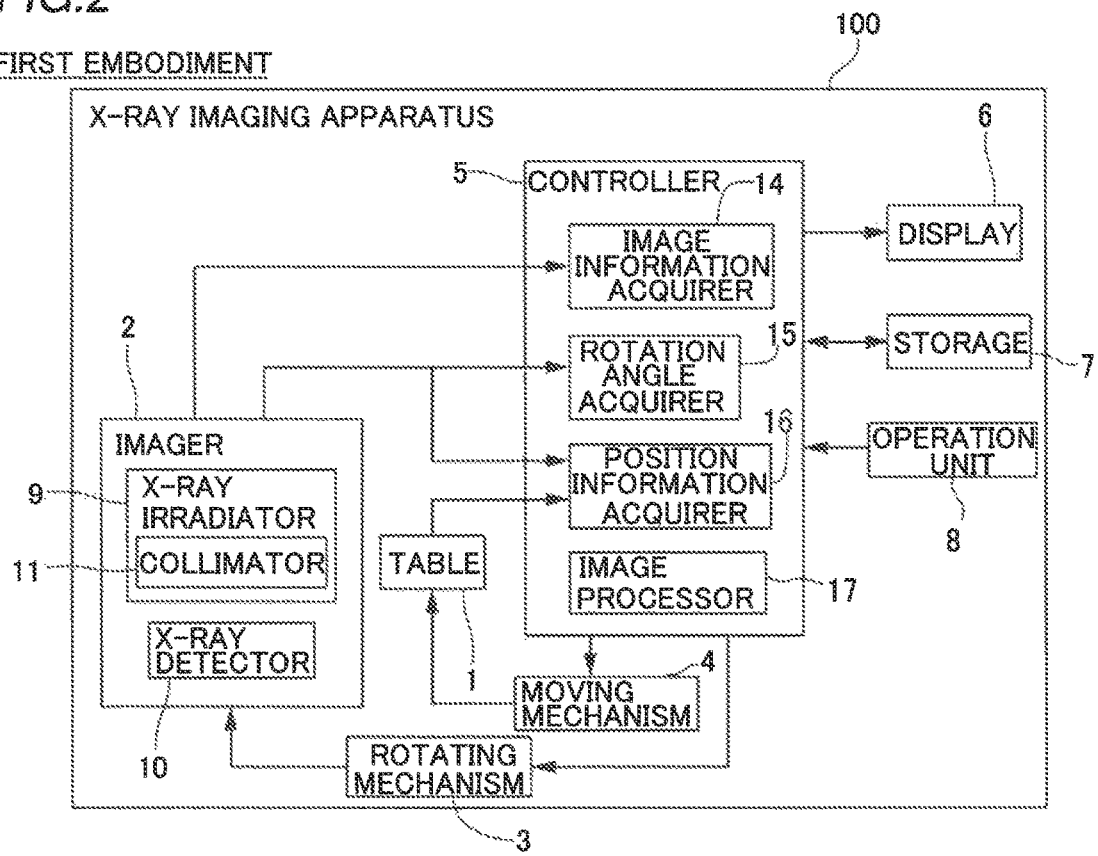
FIG. 2 is a block diagram showing the overall configuration of the X-ray imaging apparatus according to the first embodiment.

As shown in FIG. 2, the image information acquirer 14 is configured to acquire image information captured by the imager 2 from the X-ray detector 10. The image information acquired by the image information acquirer 14 is stored in the storage 7. The image information acquired by the image information acquirer 14 is used for generation of the X-ray images 40 by the image processor 17.

As shown in FIG. 2, the rotation angle acquirer 15 is configured to acquire the rotation angle 52 (see FIG. 5) of the imager 2 rotated by the rotating mechanism 3. Note that the rotation angle 52 of the imager 2 is an angle defined by a vertical direction and the optical axis 22 (see FIG. 5) of the X-rays.

The position information acquirer 16 is configured to acquire position information of the table 1 moved by the moving mechanism 4, as shown in FIG. 2. The position information of the table 1 includes coordinate information (X, Y, and Z) at a predetermined position of the table 1. For example, the position information of the table 1 includes coordinate information (X, Y, and Z) at any position in the vicinity of the four corners of the table 1. Thus, the position information acquirer 16 can acquire the amount of movement of the table 1 relatively moved, using the coordinate information of the table 1 as the position information of the table 1.

As shown in FIG. 2, the image processor 17 is configured to generate the X-ray images 40 based on the image information acquired by the image information acquirer 14. The image processor 17 is configured to generate a long image 41 (see FIG. 4) based on a plurality of X-ray images 40 captured with the imager 2 inclined with respect to the table 1. The image processor 17 includes a processor such as a graphics processing unit (GPU) or a field-programmable gate array (FPGA) configured for image processing, for example. The configuration in which the image processor 17 generates the long image 41 is described in detail below.

The display 6 is configured as a liquid crystal display, for example. The display 6 is configured to display the X-ray images 40 generated by the image processor 17 based on the image information captured by the imager 2. The display 6 is also configured to display the long image 41 generated by splicing the X-ray images 40 in the image processor 17.

The storage 7 includes a hard disk drive (HDD) or a nonvolatile memory, for example. The storage 7 stores programs used for processing of the rotating mechanism 3, the moving mechanism 4, the image information acquirer 14, the rotation angle acquirer 15, the position information acquirer 16, and the image processor 17. The storage 7 is configured to be able to store the image information captured by the imager 2, the rotation angle 52 (and the rotation angle 54 (see FIG. 6)) of the imager 2 acquired by the rotation angle acquirer 15, the position information of the table 1 acquired by the position information acquirer 16, the X-ray images 40 generated by the image processor 17, and the long image 41 generated by the image processor 17.

The operation unit 8 includes a mouse and a keyboard, for example. The operation unit 8 is configured to receive input operations from an operator. The operation unit 8 is configured to transmit the received input operations to the controller 5.

(Long Image Generation Method)

Figure 3:
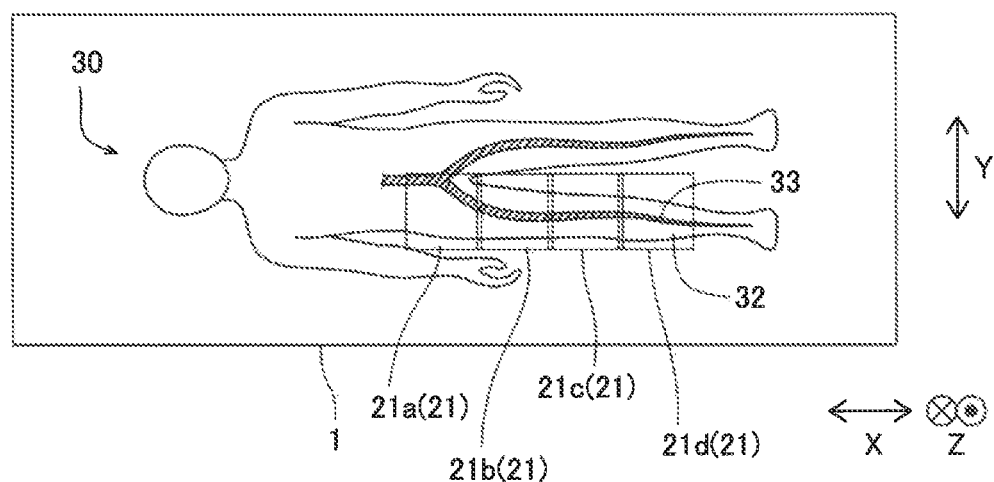
FIG. 3 is a schematic view for illustrating imaging positions for a plurality of X-ray images.

The configuration in which the image processor 17 generates the long image 41 is now described with reference to FIGS. 3 and 4.

The X-ray imaging apparatus 100 according to the first embodiment is configured to be able to perform X-ray imaging at a plurality of imaging positions 21 of the subject 30 while the moving mechanism 4 moves the table 1. Specifically, X-ray imaging is performed at the plurality of imaging positions 21, as shown in FIG. 3, by moving the table 1 in the X and Y directions with respect to the imager 2. In the first embodiment, the image information acquirer 14 acquires the image information obtained by X-ray imaging, and the position information acquirer 16 acquires the position information of the table 1. In the first embodiment, the X-ray images 40 and the long image 41 include images obtained by imaging the lower limb 32 of the subject 30. In the first embodiment, the X-ray images 40 are captured at the plurality of imaging positions 21, but FIG. 3 shows, for convenience, an example in which the X-ray imaging apparatus 100 captures the X-ray images 40 at four of the plurality of imaging positions 21 at which the X-ray images 40 are captured: a first imaging position 21a, a second imaging position 21b, a third imaging position 21c, and a fourth imaging position 21d.

Figure 4:
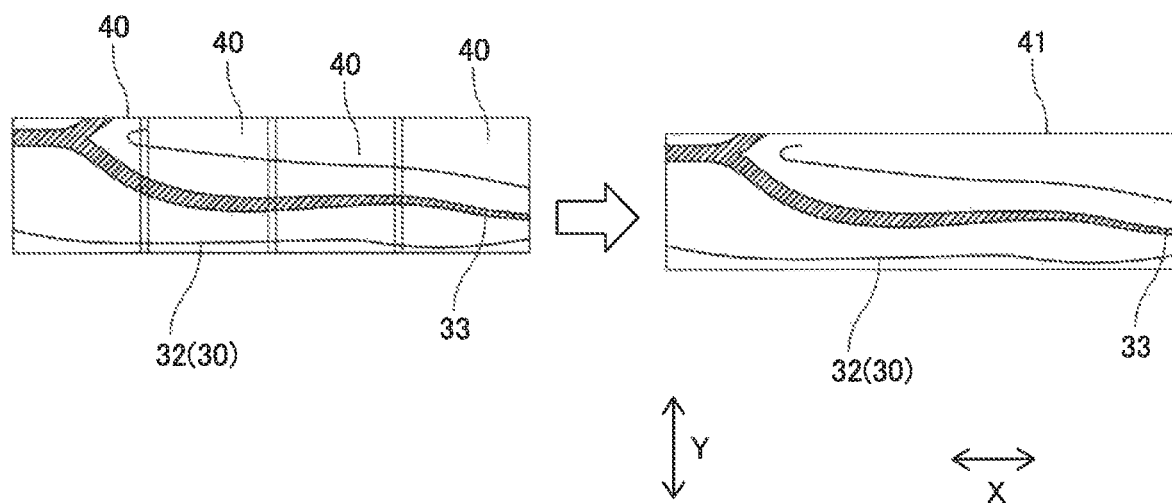
FIG. 4 is a schematic view for illustrating a long image generated by splicing the plurality of X-ray images.

As shown in FIG. 4, the image processor 17 generates the X-ray images 40 obtained by X-ray imaging at the plurality of imaging positions 21 from the image information obtained by X-ray imaging. The image processor 17 acquires the amount of movement between the X-ray images 40 based on the position information of the table 1 at the plurality of imaging positions 21, and generates the long image 41 by splicing the X-ray images 40 based on the acquired amount of movement.

When X-rays are radiated in the Z direction and imaging is performed despite the fact that in the lower limb 32, a region of interest 31 of a blood vessel 33 to be checked and a bone (not shown) overlap each other in the Z direction, the visibility of the region of interest 31 to be checked decreases. Therefore, in the first embodiment, the X-ray imaging apparatus 100 is configured to perform imaging in a state in which the optical axis 22 of the X-rays radiated from the X-ray irradiator 9 is inclined with respect to the table 1 by rotating the imager 2 with the rotating mechanism 3. Specifically, the controller 5 is configured to perform control to perform imaging at the plurality of imaging positions 21 while controlling the moving mechanism 4 to move the table 1 and the imager 2 relative to each other in at least one of the short-side direction (Y direction) or the longitudinal direction (X direction) of the table 1 in a state in which the imager 2 is inclined with respect to the table 1. In this case, the image processor 17 is configured to generate the long image 41 (see FIG. 4), which is longer than a single X-ray image 40, by performing processing of varying the magnifications of the plurality of X-ray images 40 based on the amount of relative movement of the table 1 and splicing the plurality of X-ray images 40. The imager 2 is inclined such that it is possible to image the region of interest 31 and the bone in an oblique direction with respect to the Z direction, and thus it is possible to significantly reduce or prevent a decrease in the visibility of the region of interest 31.

(Inclination of Imager)

The configuration in which the rotating mechanism 3 (see FIG. 6) rotates the imager 2 so as to incline the imager 2 with respect to the table 1 is now described with reference to FIGS. 5 and 6.

Figure 5:
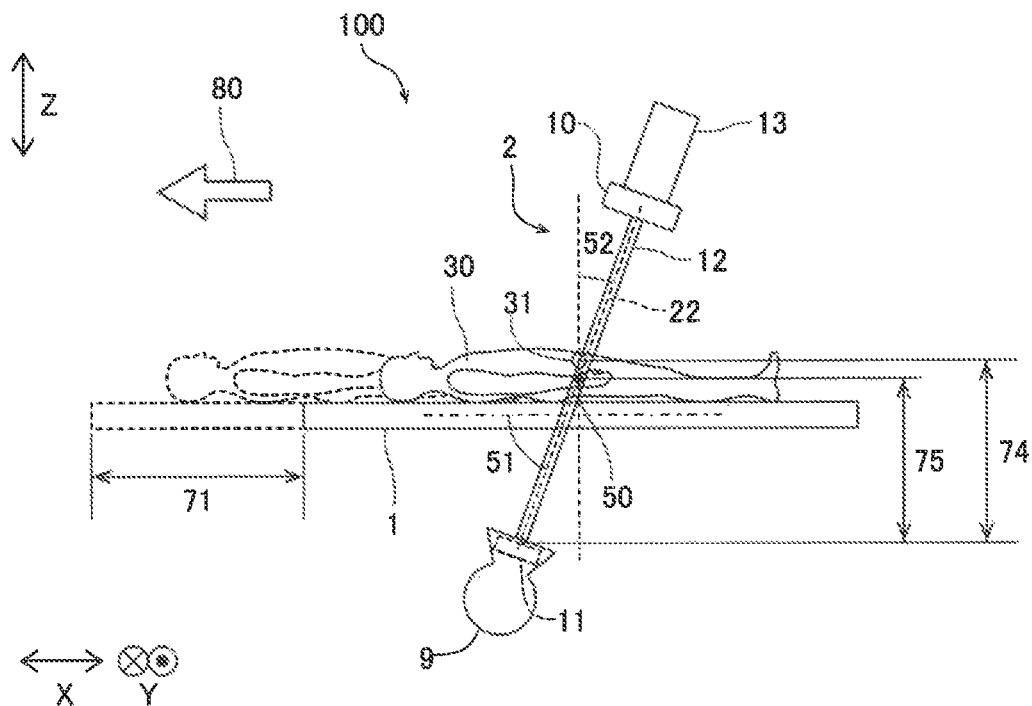
FIG. 5 is a schematic view showing the X-ray imaging apparatus according to the first embodiment, as viewed in a Y direction.

FIG. 5 is a schematic view showing a state in which the optical axis 22 of the X-rays radiated from the X-ray irradiator 9 is inclined with respect to the longitudinal direction (X direction) of the table 1 at an angle 51. In the first embodiment, as shown in FIG. 5, the rotating mechanism 3 rotates the imager 2 by the rotation angle 52 from the vertical direction such that it is possible to dispose the imager 2 in a state in which the optical axis 22 of the X-rays radiated from the X-ray irradiator 9 is inclined with respect to the longitudinal direction (X direction) of the table 1 at the angle 51. That is, the sum of the angle 51 defined by the optical axis 22 of the X-rays and the longitudinal direction (X direction) of the table 1 and the rotation angle 52 of the imager 2 is 90 degrees. Therefore, when one of the rotation angle 52 of the imager 2 and the angle 51 defined by the optical axis 22 of the X-rays and the longitudinal direction (X direction) of the table 1 is increased, the other is decreased. Note that the angle 51 defined by the optical axis 22 of the X-rays radiated from the X-ray irradiator 9 and the longitudinal direction (X direction) of the table 1 is an angle excluding 0 degrees, 90 degrees, and 180 degrees in an angle range of 0 degrees to 180 degrees.

Figure 6:
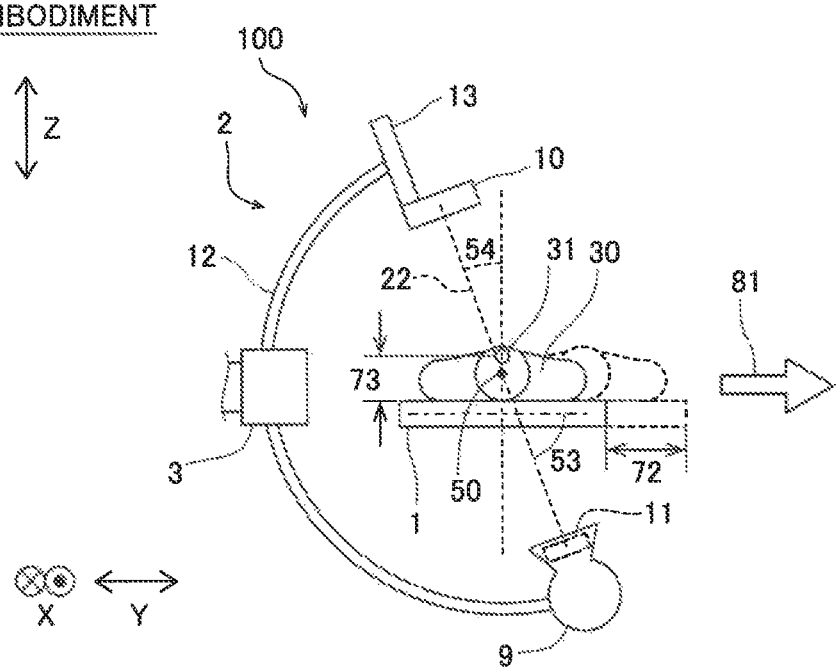
FIG. 6 is a schematic view showing the X-ray imaging apparatus according to the first embodiment, as viewed in an X direction.

FIG. 6 is a schematic view showing a state in which the optical axis 22 of the X-rays radiated from the X-ray irradiator 9 is inclined with respect to the short-side direction (Y direction) of the table 1 at an angle 53. In the first embodiment, as shown in FIG. 6, the rotating mechanism 3 rotates the imager 2 by the rotation angle 54 with respect to the vertical direction such that it is possible to dispose the imager 2 in a state in which the optical axis 22 of the X-rays radiated from the X-ray irradiator 9 is inclined with respect to the short-side direction (Y direction) of the table 1 at the angle 53. That is, the sum of the angle 53 defined by the optical axis 22 of the X-rays and the short-side direction (Y direction) of the table 1 and the rotation angle 54 of the imager 2 is 90 degrees. Accordingly, when one of the rotation angle 54 of the imager 2 and the angle 53 defined by the optical axis 22 of the X-rays and the longitudinal direction (X direction) of the table 1 is increased, the other is decreased. Note that the angle 53 defined by the optical axis 22 of the X-rays radiated from the X-ray irradiator 9 and the short-side direction (Y direction) of the table 1 is an angle excluding 0 degrees, 90 degrees, and 180 degrees in an angle range of 0 degrees to 180 degrees.

In the first embodiment, the table 1 is moved along arrow 80 in a state in which the optical axis 22 of the X-rays is inclined with respect to the longitudinal direction (X direction) of the table 1, as shown in FIG. 5, and the table 1 is moved along arrow 81 in a state in which the optical axis 22 of the X-rays is inclined with respect to the short-side direction (Y direction) of the table 1, as shown in FIG. 6, so as to capture the X-ray images 40 at the plurality of imaging positions 21. When the table 1 is moved in a state in which the optical axis 22 of the X-rays is inclined with respect to the table 1, the magnification may vary between the X-ray images 40 depending on the inclination direction of the optical axis 22 of the X-rays and the moving direction of the table 1. That is, when the table 1 is moved in the longitudinal direction (X direction) of the table 1 in a state in which the optical axis 22 of the X-rays is inclined with respect to the longitudinal direction (X direction) of the table 1, and when the table 1 is moved in the short-side direction (Y direction) of the table 1 in a state in which the optical axis 22 of the X-rays is inclined with respect to the short-side direction (Y direction) of the table 1, the magnification varies between the X-ray images 40. When the table 1 is moved in the short-side direction (Y direction) of the table 1 in a state in which the optical axis 22 of the X-rays is inclined with respect to the longitudinal direction (X direction) of the table 1, and when the table 1 is moved in the longitudinal direction (X direction) of the table 1 in a state in which the optical axis 22 of the X-rays is inclined with respect to the short-side direction (Y direction) of the table 1, the magnifications of the X-ray images 40 do not vary.

Figure 7:
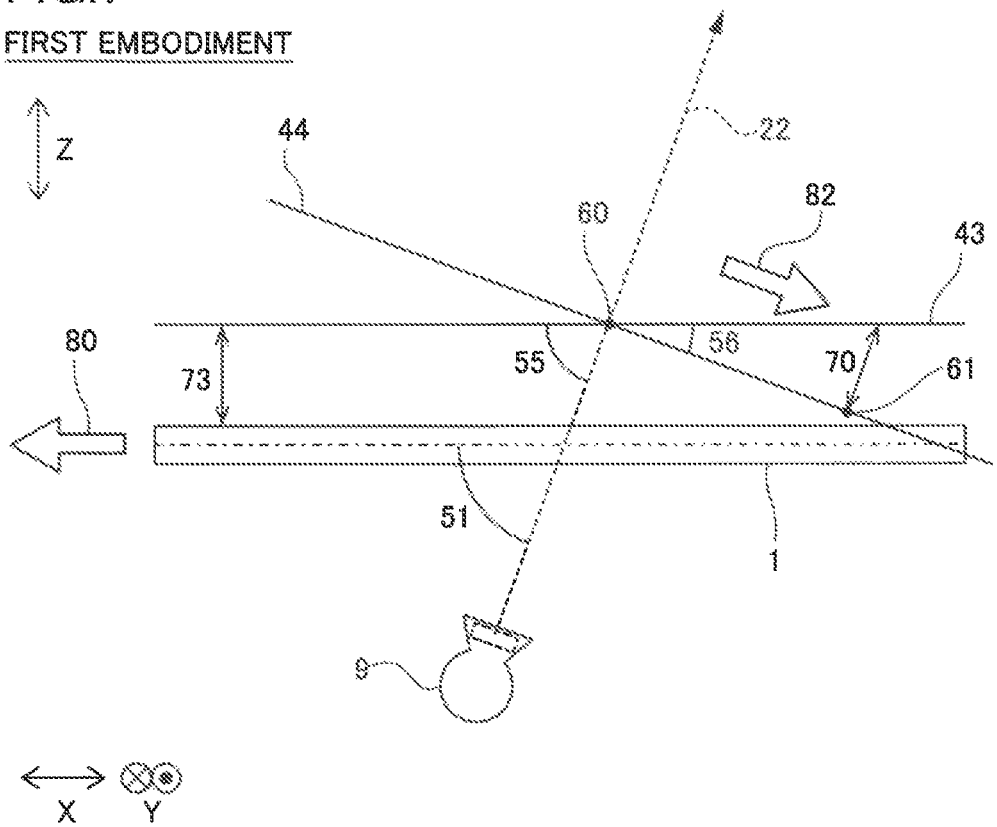
FIG. 7 is a schematic view for illustrating a variation in magnification that occurs in the plurality of X-ray images.

A variation in magnification between the X-ray images 40 is now described with reference to FIG. 7. FIG. 7 shows an example in which the imager 2 is inclined with respect to the table 1 in the longitudinal direction at the angle 51 by rotating the imager 2 by the rotation angle 52 with respect to the vertical direction. A straight line 43 in FIG. 7 is a straight line indicating the height position of the region of interest 31 of the subject 30. The straight line 43 extends in the longitudinal direction (X direction) of the table 1, and is parallel to the table 1. A straight line 44 in FIG. 7 is an imaging plane 44 parallel to the detection surface of the X-ray detector 10. When imaging is performed without inclining the imager 2, the imaging plane 44 is parallel to the straight line 43. That is, when imaging is performed without inclining the imager 2, the imaging plane 44 is parallel to the table 1. However, when imaging is performed with the imager 2 inclined, the straight line 43 indicating the height position of the region of interest 31 of the subject 30 and the imaging plane 44 are inclined at the rotation angle 52. An angle 55 defined by the straight line 43 and the optical axis 22 of the X-rays is the same as the angle 51 of the imager 2 with respect to the table 1 in the longitudinal direction. In addition, an angle 56 defined by the straight line 43 and the imaging plane 44 is the same as the rotation angle 52 of the imager 2.

When the table 1 is relatively moved in a state in which the straight line 43 indicating the height position of the region of interest 31 of the subject 30 and the imaging plane 44 are inclined at the rotation angle 52, a distance 70 between the straight line 43 indicating the height position of the region of interest 31 of the subject 30 and the imaging plane 44 varies between the X-ray images 40. A variation in the distance 70 between the straight line 43 indicating the height position of the region of interest 31 of the subject 30 and the imaging plane 44 is described using pixels 60 included in the X-ray images 40.

A pixel 60 shown in FIG. 7 is a pixel at a point at which the straight line 43 indicating the height position of the region of interest 31 of the subject 30 and the imaging plane 44 intersect with each other among pixels included in an X-ray image 40 captured at a certain imaging position 21. When the table 1 is moved along arrow 80, the pixel 60 moves along arrow 82 on the imaging plane 44. Specifically, the pixel 60 moves to a position indicated by a pixel 61 on the imaging plane 44. The imaging plane 44 is inclined with respect to the straight line 43 indicating the height position of the region of interest 31 of the subject 30, and thus the path length of an X-ray, which has been transmitted through a position of the subject 30 corresponding to the pixel 60, varies. That is, when the pixel 60 moves to the position of the pixel 61, the distance 70 between the straight line 43 indicating the height position of the region of interest 31 of the subject 30 and the imaging plane 44 varies. The distance 70 varies similarly for the other pixels in the X-ray image 40, and thus the magnification at the region of interest 31 varies between the X-ray images 40.

The example shown in FIG. 7 shows a state in which the optical axis 22 of the X-rays radiated from the X-ray irradiator 9 is inclined with respect to the longitudinal direction (X direction) of the table 1 at the angle 51, but also when the table 1 is moved along arrow 81 in a state in which the optical axis 22 of the X-rays radiated from the X-ray irradiator 9 is inclined with respect to the short-side direction (Y direction) of the table 1 at the angle 53, the magnification varies between the X-ray images 40 as in the example shown in FIG. 7.

Long Image in Comparative Example

Figure 8:
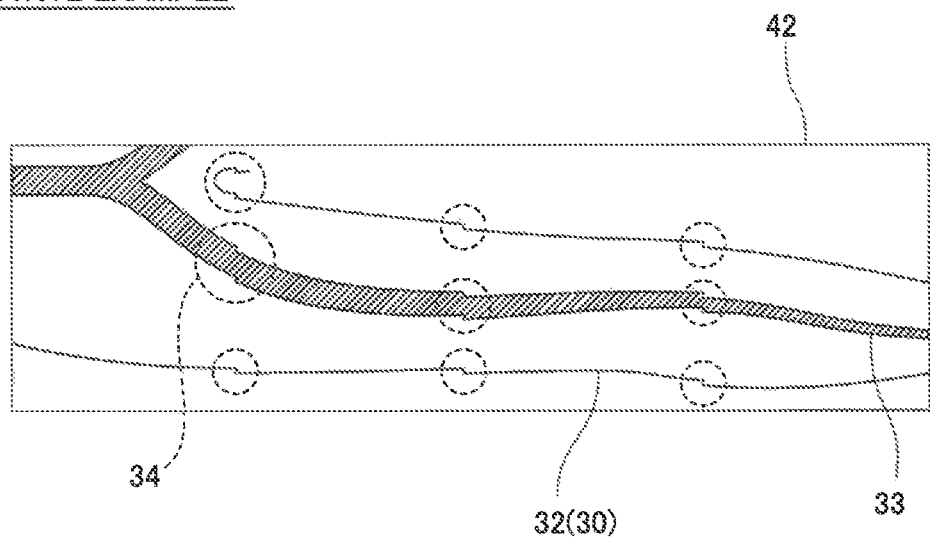
FIG. 8 is a schematic view for illustrating a long image in Comparative Example.

A long image 42 in Comparative Example is now described with reference to FIG. 8. As Comparative Example, an example is shown in which the long image 42 is generated by splicing a plurality of X-ray images 40 captured with the imager 2 rotated by the rotation angle 52 from the vertical direction (see FIG. 5) based only on the position information of the table 1.

When the table 1 is moved along arrow 80 in a state in which the optical axis 22 of the X-rays radiated from the X-ray irradiator 9 is inclined at the rotation angle 52 from the vertical direction, the magnification at the region of interest 31 in each of the plurality of X-ray images 40 varies between the images. Therefore, in Comparative Example in which the long image 42 is generated by splicing the X-ray images 40 based only on the position information of the table 1, the X-ray images 40 are not appropriately spliced at seams of the X-ray images 40. The expression that the X-ray images 40 are not appropriately spliced at seams of the X-ray images 40 refers to a state in which steps are generated at connections of the blood vessel 33, as in regions 34 surrounded by broken-line circles in the long image 42 shown in FIG. 8.

(Variation in Magnification of X-Ray Image)

Therefore, in the first embodiment, the image processor 17 is configured to perform processing of varying the magnifications of the plurality of X-ray images 40 based on at least one of the angle 51 defined by the optical axis 22 of the X-rays radiated from the X-ray irradiator 9 and the longitudinal direction of the table 1 or the angle 53 defined by the optical axis 22 of the X-rays radiated from the X-ray irradiator 9 and the short-side direction of the table 1, both of which are formed when the optical axis 22 of the X-rays radiated from the X-ray irradiator 9 is inclined with respect to the table 1, and the amount of relative movement of the table 1, and splicing the plurality of X-ray images 40.

Specifically, as shown in FIGS. 5 and 6, the image processor 17 acquires the magnifications of the plurality of X-ray images 40 based on the rotation angle 52 of the imager 2 rotated such that the optical axis 22 of the X-rays radiated from the X-ray irradiator 9 is inclined with respect to the longitudinal direction of the table 1 at the angle 51, the rotation angle 54 of the imager 2 rotated such that the optical axis 22 of the X-rays radiated from the X-ray irradiator 9 is inclined with respect to the short-side direction of the table 1 at the angle 53, and the amount of relative movement (Vectorn [pixel]) of the table 1 between the X-ray images 40.

In the first embodiment, when generating the long image 41, the image processor 17 converts Vectorn [mm] from a millimeter unit to Vectorn [pixel] of a pixel unit. Known processing can be applied to processing of converting Vectorn [mm] from a millimeter unit to Vectorn [pixel] of a pixel unit, and thus detailed description thereof is omitted. The image processor 17 generates the long image 41 by splicing the plurality of X-ray images 40 based on the converted Vectorn [pixel] and the magnifications of the X-ray images 40.

The image processor 17 acquires the magnifications of the X-ray images 40 based on a vertical distance 74 (see FIG. 5) between the X-ray irradiator 9 and the subject 30 (region of interest 31) at the imaging position 21 at which each of the X-ray images 40 is captured, a vertical distance 75 (see FIG.

5) between the X-ray irradiator 9 and the rotation center 50 of the rotating mechanism 3 at the imaging position 21 at which each of the X-ray images 40 is captured, and the distance 70 (see FIG. 7) between the imaging plane 44 and the height position of the region of interest 31 of the subject 30 at the imaging position 21 at which each of the X-ray images 40 is captured.

In the first embodiment, the image processor 17 is configured to perform processing of varying the magnifications of the plurality of X-ray images 40 based on the amount of relative movement (Vectorn [pixel]) of the table 1 and splicing the plurality of X-ray images 40 when imaging is performed while the table 1 is moved in the longitudinal direction of the table 1 in a state in which the optical axis 22 of the X-rays radiated from the X-ray irradiator 9 is inclined with respect to the longitudinal direction (X direction) of the table 1, and when imaging is performed while the table 1 is moved in the short-side direction of the table 1 in a state in which the optical axis 22 of the X-rays radiated from the X-ray irradiator 9 is inclined with respect to the short-side direction of the table 1. Note that the long image 41 shown in FIG. 4 is an example of a long image generated from a plurality of X-ray images 40 captured while the table 1 is moved in the longitudinal direction of the table 1 in a state in which the optical axis 22 of the X-rays is inclined with respect to the longitudinal direction (X direction) of the table 1 at the angle 51. Furthermore, the long image 41 shown in FIG. 4 is an example of a long image generated from a plurality of X-ray images 40 captured while the table 1 is moved in the longitudinal direction of the table 1 in a state in which the optical axis 22 of the X-rays is not inclined with respect to the short-side direction (Y direction) of the table 1 at the angle 53.

In the first embodiment, the image processor 17 is configured to vary the magnifications of the plurality of X-ray images 40 such that the distance 70 between the imaging plane 44 parallel to the detection surface of the X-ray detector 10 and the height position of the region of interest 31 of the subject 30 is the same between the X-ray images 40. Specifically, the image processor 17 acquires a ratio of the magnification of an X-ray image 40, which is desired to be varied, to the magnification of a reference X-ray image 40 (a first X-ray image 40, for example), and divides the magnification of the X-ray image 40, the magnification of which is desired to be varied, by the acquired ratio to vary the magnification of the X-ray image 40.

In the first embodiment, the image processor 17 is configured to acquire the magnification for each of the X-ray images 40 based on the distance 70 between the imaging plane 44 and the height position of the region of interest 31 of the subject 30 that occurs due to imaging with the imager 2 rotated to be inclined with respect to the table 1, and to generate the long image 41 while varying the magnifications of the plurality of X-ray images 40 based on a variation in the distance 70 between the imaging plane 44 and the height position of the region of interest 31 of the subject 30 that occurs due to movement of the table 1 relative to the imager 2 in at least one of the short-side direction (Y direction) or the longitudinal direction (X direction) of the table 1 in a state in which the imager 2 is rotated to be inclined with respect to the table 1.

The image processor 17 is configured to acquire the distance 70 between the imaging plane 44 and the height position of the region of interest 31 of the subject 30 based on the moving distance 71 (or the moving distance 72) of the table 1 at each imaging position 21 and the rotation angle 52 (or the rotation angle 54) of the imager 2. The distance 70 between the imaging plane 44 and the height position of the region of interest 31 of the subject 30 may be set in advance by a user. Alternatively, the distance 70 may be input by the user each time imaging is performed. When the distance 70 between the imaging plane 44 and the height position of the region of interest 31 of the subject 30 is set in advance by the user, the distance 70 between the imaging plane 44 and the height position of the region of interest 31 of the subject 30 is stored in the storage 7. In the first embodiment, the height position of the region of interest 31 of the subject 30 can be set. The image processor 17 is configured to acquire the magnification for each of the X-ray images 40 based on the distance 70 between the imaging plane 44 and the set height position of the region of interest 31 of the subject 30.

Figure 9:
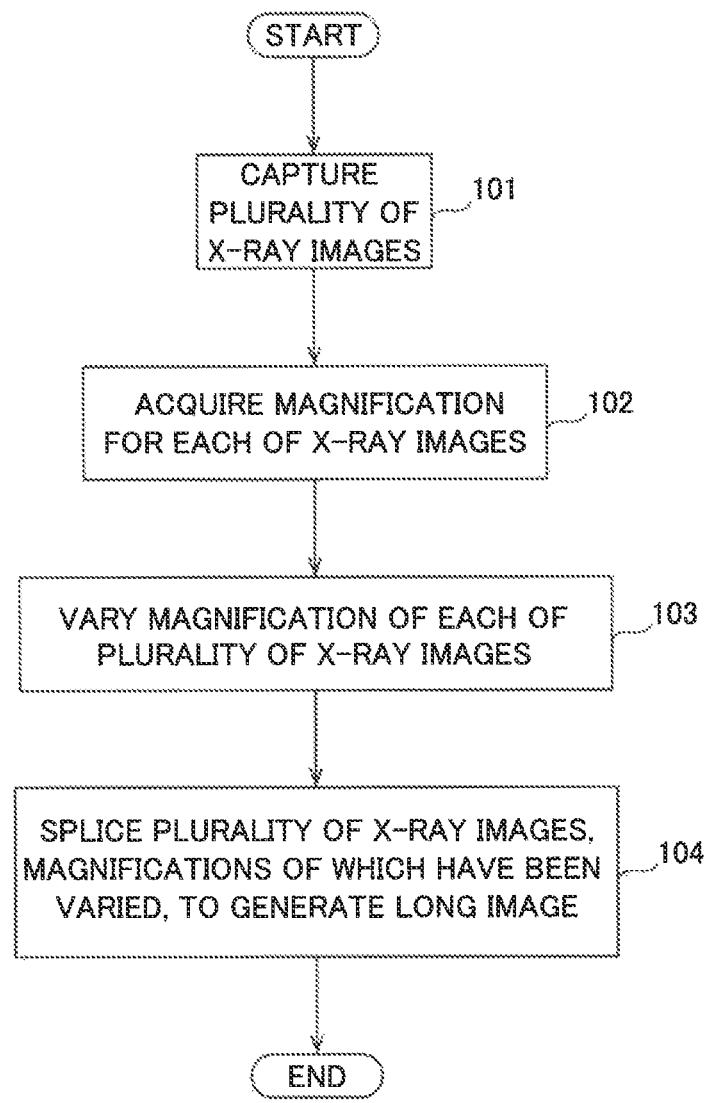
FIG. 9 is a flowchart for illustrating long image generation processing in the X-ray imaging apparatus according to the first embodiment.

Processing of generating the long image 41 in the X-ray imaging apparatus 100 according to the first embodiment is now described with reference to FIG. 9.

In step 101, the controller 5 controls the rotating mechanism 3, the moving mechanism 4, and the imager 2 to capture the X-ray images 40 at the plurality of imaging positions 21 while moving the table 1 in a state in which the imager 2 is inclined. Thereafter, the processing advances to step 102.

In step 102, the image processor 17 acquires the magnification for each X-ray image 40. Thereafter, the processing advances to step 103.

In step 103, the image processor 17 varies the magnification of each of the plurality of X-ray images 40. Thereafter, the processing advances to step 104.

In step 104, the image processor 17 splices the plurality of X-ray images 40, the magnifications of which have been varied, to generate the long image 41, and the processing is terminated.

Advantages of First Embodiment

According to the first embodiment, the following advantages are obtained.

According to the first embodiment, as described above, the X-ray imaging apparatus 100 includes the table 1 on which the subject 30 is placed, the imager 2 including the X-ray irradiator 9 configured to irradiate the subject 30 with X-rays and the X-ray detector 10 configured to detect the X-rays radiated from the X-ray irradiator 9 and transmitted through the subject 30, the imager 2 being configured to capture the X-ray images 40, the rotating mechanism 3 configured to rotate the imager 2, the moving mechanism 4 configured to move so as to change the relative position of the table 1 to the imager 2, and the image processor 17 configured to generate the long image 41, which is longer than a single X-ray image 40, by performing the processing of varying the magnifications of the plurality of X-ray images 40 based on the amount of relative movement of the table 1 and splicing the plurality of X-ray images 40 when imaging is performed at the plurality of imaging positions 21 while the table 1 is moved relative to the imager 2 in at least one of the short-side direction (Y direction) or the longitudinal direction (X direction) of the table 1 in a state in which the imager 2 is rotated such that the optical axis 22 of the X-rays radiated from the X-ray irradiator 9 is inclined with respect to the table 1.

When imaging is performed with the imager 2 inclined, an X-ray is incident on the table 1 in an oblique direction. Therefore, the path length (distance 70) of the X-ray, which has been transmitted through the subject 30, to the X-ray detector 10 differs depending on a location in the X-ray images 40. Therefore, as compared with the case in which imaging is performed without inclining the imager 2, regions having different sizes are generated in the X-ray images 40. In addition, the path length of the X-ray, which has been transmitted through the subject 30, to the X-ray detector 10 differs depending on a location in the X-ray images 40, and thus the magnification at the same region of the subject 30 varies between the X-ray images 40 when imaging is performed while the imager 2 is moved in an inclined state. Thus, when the X-ray images 40 are spliced, steps are generated at seams of the X-ray images 40. Therefore, with the above configuration, the processing of varying the magnifications of the plurality of X-ray images 40 based on the amount of relative movement (Vectorn [pixel]) of the table 1 and splicing the plurality of X-ray images 40 is performed, and thus it becomes possible to match the magnifications of the subject 30 that appears at the seams between the X-ray images 40, and the X-ray images 40 can be appropriately spliced. Consequently, even when the long image 41 is generated by splicing the plurality of X-ray images 40 captured while changing the imaging position 21 in a state in which the imager 2 is inclined, the long image 40 in which the X-ray images 40 are appropriately spliced can be generated.

According to the first embodiment, as described above, the image processor 17 is configured to acquire the magnifications of the plurality of X-ray images 40 based on at least one of the angle 51 defined by the optical axis 22 of the X-rays radiated from the X-ray irradiator 9 and the longitudinal direction (X direction) of the table 1 or the angle 53 defined by the optical axis 22 of the X-rays radiated from the X-ray irradiator 9 and the short-side direction (Y direction) of the table 1, both of which are formed when the optical axis 22 of the X-rays radiated from the X-ray irradiator 9 is inclined with respect to the table 1, and the amount of relative movement of the table 1. The angle 51 defined by the optical axis 22 of the X-rays radiated from the X-ray irradiator 9 and the longitudinal direction of the table 1, and the angle 53 defined by the optical axis 22 of the X-rays radiated from the X-ray irradiator 9 and the short-side direction of the table 1 are known values at the time of starting imaging. Therefore, with the above configuration, the magnification of each of the X-ray images 40 can be easily varied by acquiring the amount of relative movement (Vectorn [pixel]) of the table 1.

According to the first embodiment, as described above, the image processor 17 is configured to perform the processing of varying the magnifications of the plurality of X-ray images 40 based on the amount of relative movement of the table 1 and splicing the plurality of X-ray images 40 when imaging is performed while the table 1 is moved in the longitudinal direction of the table 1 in a state in which the optical axis 22 of the X-rays radiated from the X-ray irradiator 9 is inclined with respect to the longitudinal direction of the table 1, and when imaging is performed while the table 1 is moved in the short-side direction of the table 1 in a state in which the optical axis 22 of the X-rays radiated from the X-ray irradiator 9 is inclined with respect to the short-side direction of the table 1. Accordingly, even when the magnifications of the plurality of X-ray images 40 are different from each other, the X-ray images 40 can be appropriately spliced. Consequently, imaging is performed while the table 1 is relatively moved in a state in which the imager 2 is inclined such that even when the magnifications of the X-ray images 40 are different from each other, an appropriate long image 41 can be generated.

According to the first embodiment, as described above, the image processor 17 is configured to vary the magnifications of the plurality of X-ray images 40 such that the distance 70 between the imaging plane 44 parallel to the detection surface of the X-ray detector 10 and the height position of the region of interest 31 of the subject 30 is the same between the X-ray images 40. Accordingly, with the distance 70 between the imaging plane 44 of any of the plurality of X-ray images 40 and the height position of the region of interest 31 of the subject 30 as a reference, the distances 70 between the imaging planes 44 of the other X-ray images 40 and the height position of the region of interest 31 of the subject 30 can be the same as the reference distance 70. Consequently, the X-ray images 40 can be appropriately spliced using any of the plurality of X-ray images 40 as a reference.

According to the first embodiment, as described above, the image processor 17 is configured to acquire the magnification for each of the X-ray images 40 based on the distance 70 between the imaging plane 44 and the height position of the region of interest 31 of the subject 30 that occurs due to imaging with the imager 2 rotated to be inclined with respect to the table 1, and to generate the long image 41 while varying the magnifications of the plurality of X-ray images 40 based on a variation in the distance 70 between the imaging plane 44 and the height position of the region of interest 31 of the subject 30 that occurs due to movement of the table 1 relative to the imager 2 in at least one of the short-side direction or the longitudinal direction of the table 1 in a state in which the imager 2 is rotated to be inclined with respect to the table 1. Accordingly, the distances 70 between the imaging planes 44 of the plurality of X-ray images 40 and the height position of the region of interest 31 of the subject 30 are compared with each other such that a difference between the magnifications of the X-ray images 40 can be easily acquired. Consequently, the magnification of each of the X-ray images 40 can be easily varied, and the long image 41 in which the X-ray images 40 are appropriately spliced can be easily acquired.

According to the first embodiment, as described above, the X-ray imaging apparatus 100 further includes the rotation angle acquirer 15 configured to acquire the rotation angle 52 and the rotation angle 54 of the imager 2, and the position information acquirer 16 configured to acquire the position information of the table 1, and the image processor 17 is configured to acquire the distance 70 between the imaging plane 44 and the height position of the region of interest 31 of the subject 30 based on the moving distance 71 and the moving distance 72 of the table 1 at each imaging position 21 and the rotation angle 52 and the rotation angle 54 of the imager 2. The rotation angle 52 and the rotation angle 54 of the imager 2 and the height position of the region of interest 31 of the subject 30 are values set in advance when imaging is performed, and thus the same are known values. Therefore, with the above configuration, the moving distance 71 and the moving distance 72 of the table 1 at each imaging position 21 are acquired such that the distance 70 between the imaging plane 44 and the height position of the region of interest 31 of the subject 30 can be easily acquired.

According to the first embodiment, as described above, the height position of the region of interest 31 of the subject 30 is settable, and the image processor 17 is configured to acquire the magnification for each of the X-ray images 40 based on the distance 70 between the imaging plane 44 and the set height position of the region of interest 31 of the subject 30. Accordingly, even when the height position of the region of interest 31 of the subject 30 is changed, the magnification of each of the X-ray images 40 can be acquired based on the changed height position of the region of interest 31 of the subject 30. Consequently, it is possible to generate the long image 41 at the height position of the region of interest 31 that the user desires to check, and thus convenience for the user can be improved.

According to the first embodiment, as described above, the X-ray images 40 and the long image 41 include images obtained by imaging the lower limb 32 of the subject 30. The long image 41 is generally generated when the lower limb 32 of the subject 30 is radiographed, and thus it is particularly effective to apply the present invention to the X-ray imaging apparatus 100 that images the blood vessel 33 of the lower limb 32 with the imager 2 inclined with respect to the table 1.

Second Embodiment

A second embodiment is now described with reference to FIGS. 5, 6, 10, and 11. Unlike the first embodiment in which the subject 30 is imaged by one imager 2, in the second embodiment, an imager 2 includes a first imager 2a (see FIG. 10) and a second imager 2b (see FIG. 10) that captures a plurality of X-ray images 40 in a state in which the imager 2b is inclined at an angle different from that of the first imager 2a with respect to the subject 30. In the figures, the same configurations as those of the first embodiment are denoted by the same reference numerals. Also in the second embodiment, as shown in FIG. 5 or 6, the imager 2 is inclined with respect to a table 1.

Figure 10:
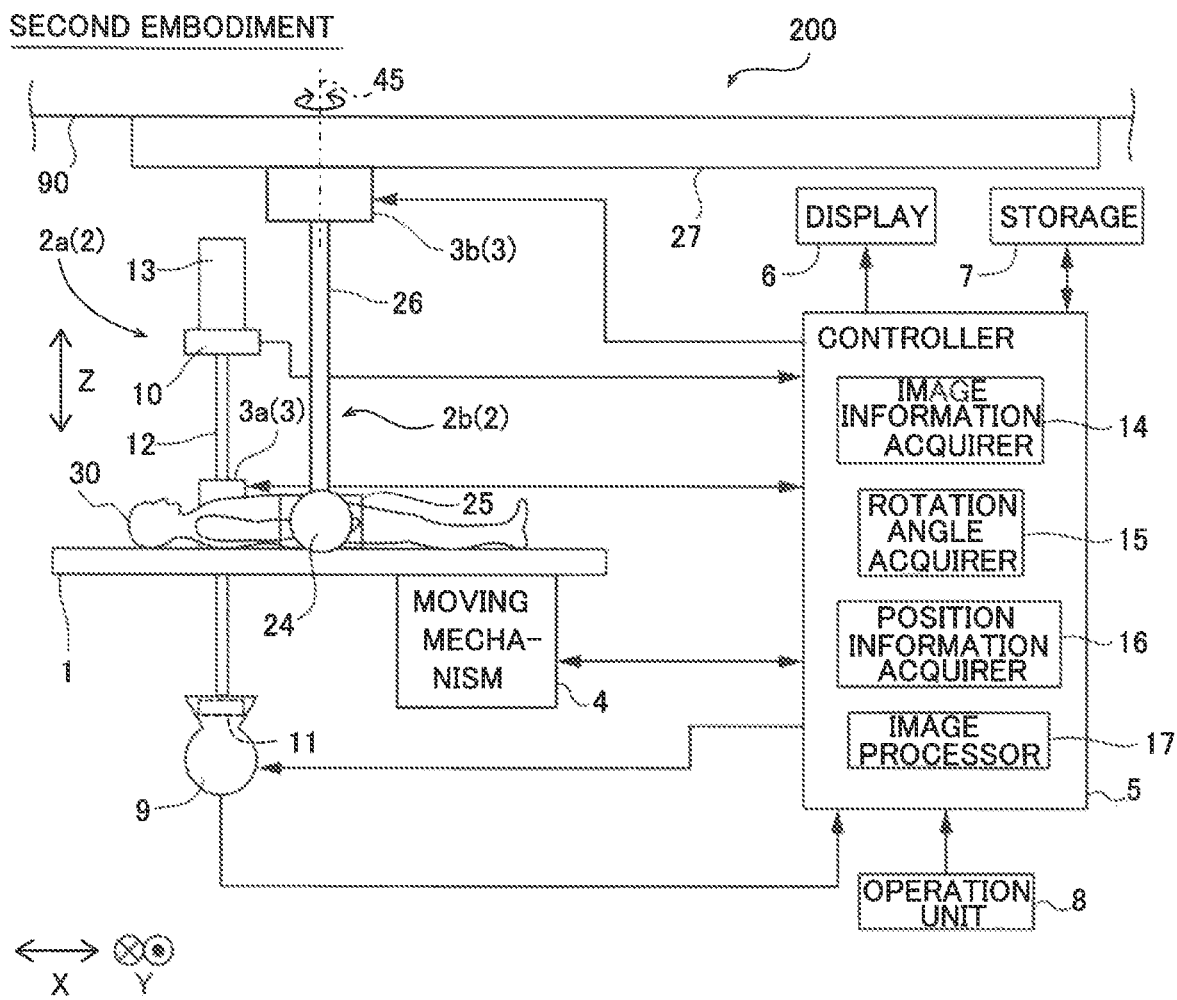
FIG. 10 is a schematic view showing the overall configuration of an X-ray imaging apparatus according to a second embodiment.

As shown in FIG. 10, in an X-ray imaging apparatus 200 according to the second embodiment, the imager 2 includes the first imager 2a and the second imager 2b configured to capture the plurality of X-ray images 40 in a state in which the second imager 2b is inclined at the angle different from that of the first imager 2a with respect to the subject 30. The first imager 2a is disposed in such a manner as to interpose the table 1 in a Z direction. Moreover, the second imager 2b is disposed in such a manner as to interpose the table 1 in a Y direction. In the X-ray imaging apparatus 200 according to the second embodiment, a rotating mechanism 3 includes a first rotating mechanism 3a that can rotate the first imager 2a and a second rotating mechanism 3b that can rotate the second imager 2b.

The first imager 2a includes an X-ray irradiator 9 and an X-ray detector 10. The second imager 2b includes an X-ray irradiator 24 and an X-ray detector 25. The X-ray irradiator 24 includes a collimator 28. The X-ray irradiator 24, the X-ray detector 25, and the collimator 28 have the same configurations as those of the X-ray irradiator 9, the X-ray detector 10, and the collimator 11 in the first embodiment, respectively, and thus detailed description thereof is omitted.

The first rotating mechanism 3a has the same configuration as that of the rotating mechanism 3 in the first embodiment, and thus detailed description thereof is omitted.

The second rotating mechanism 3b holds the second imager 2b via a C-shaped arm 26. The second rotating mechanism 3b is configured to be able to rotate the second imager 2b by rotating the arm 26. The second rotating mechanism 3b includes a moving mechanism configured to move the arm 26 along the outer periphery of an arm 12. The second rotating mechanism 3b is held by a moving mechanism 27 provided on a ceiling 90. The moving mechanism 27 is configured to be able to move the second rotating mechanism 3b in an X direction. Furthermore, the moving mechanism 27 is configured to be able to rotate the second rotating mechanism 3b around an axis 45.

As shown in FIG. 11, in the second embodiment, an image information acquirer 14 is configured to acquire image information captured by the first imager 2a from the X-ray detector 10. Furthermore, the image information acquirer 14 according to the second embodiment is configured to acquire image information captured by the second imager 2b from the X-ray detector 25. In the second embodiment, a rotation angle acquirer 15 is configured to acquire the rotation angle of the first imager 2a and the rotation angle of the second imager 2b.

In the second embodiment, the image processor 17 is configured to generate the X-ray images 40 captured by the first imager 2a and the X-ray images 40 captured by the second imager 2b based on the image information acquired by the image information acquirer 14. In the second embodiment, the image processor 17 is configured to generate a long image 41 by performing processing of varying the magnifications of the plurality of X-ray images 40 captured by the first imager 2a and splicing the plurality of X-ray images 40, and to generate a long image 41 by performing processing of varying the magnifications of the plurality of X-ray images 40 captured by the second imager 2b and splicing the plurality of X-ray images 40.

Processing of generating the long image 41 in the X-ray imaging apparatus 200 according to the second embodiment is now described with reference to FIG. 12.

In step 201, the controller 5 controls the moving mechanism 4, the imager 2 (the first imager 2a and the second imager 2b), and the rotating mechanism 3 (the first rotating mechanism 3a and the second rotating mechanism 3b) to capture the X-ray images 40 at a plurality of imaging positions 21 while moving the table 1 in a state in which the imager 2 (the first imager 2a and the second imager 2b) is inclined. Thereafter, the processing advances to step 202. The first imager 2a and the second imager 2b may capture the X-ray images 40 at the plurality of imaging positions 21 different from each other. Furthermore, the first imager 2a and the second imager 2b may capture the X-ray images 40 at the common imaging positions 21.

In step 202, the image processor 17 acquires the magnification for each X-ray image 40 captured by each of the first imager 2a and the second imager 2b. Thereafter, the processing advances to step 203. The first imager 2a may capture the number of X-ray images different from that of the second imager 2b. In addition, the first imager 2a may capture the same number of X-ray images as that of the second imager 2b.

In step 203, the image processor 17 varies the magnifications of the plurality of X-ray images 40 captured by each of the first imager 2a and the second imager 2b. Thereafter, the processing advances to step 204.

In step 204, the image processor 17 generates the long image 41 by splicing the plurality of X-ray images 40 captured by the first imager 2a, the magnifications of which have been varied, and generates the long image 41 by splicing the plurality of X-ray images 40 captured by the second imager 2b, the magnifications of which have been varied. Then, the processing is terminated. The configuration in which the image processor 17 generates the long image 41 is similar to the configuration according to the first embodiment, and thus detailed description thereof is omitted.

The remaining configurations of the X-ray imaging apparatus 200 according to the second embodiment are similar to those of the X-ray imaging apparatus 100 according to the remaining first embodiment.

Advantages of Second Embodiment

According to the second embodiment, as described above, the imager 2 includes the first imager 2a and the second imager 2b configured to capture the plurality of X-ray images 40 in a state in which the second imager 2b is inclined at the angle different from that of the first imager 2a with respect to the subject 30, the rotating mechanism 3 includes the first rotating mechanism 3a configured to rotate the first imager 2a, and the second rotating mechanism 3b configured to rotate the second imager 2b, and the image processor 17 is configured to generate the long image 41 by performing the processing of varying the magnifications of the plurality of X-ray images 40 captured by the first imager 2a and splicing the plurality of X-ray images 40, and to generate the long image 41 by performing the processing of varying the magnifications of the plurality of X-ray images 40 captured by the second imager 2b and splicing the plurality of X-ray images 40. Accordingly, the long images 41 captured from the angles different from each other can be acquired by the first imager 2a and the second imager 2b with a single administration of a contrast agent. Consequently, it is possible to significantly reduce or prevent an increase in the number of administrations of the contrast agent as compared with the configuration in which the contrast agent is administered a plurality of times and one imager captures images while changing the imaging angles. Furthermore, the imaging time can be reduced, and thus the amount of radiation exposure can be decreased.

The remaining advantages of the second embodiment are similar to those of the aforementioned first embodiment.

MODIFIED EXAMPLES

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the controller 5 is configured or programmed to control the moving mechanism 4 to move the table 1 in the X direction and the Y direction with respect to the imager 2 in each of the aforementioned first and second embodiments, the present invention is not limited to this. For example, a moving mechanism that can move the imager 2 may alternatively be provided, and the controller 5 may alternatively be configured or programmed to control the moving mechanism to move the imager 2 in the X direction and the Y direction with respect to the table 1.

While the image processor 17 is configured to perform the processing of varying the magnifications of the plurality of X-ray images 40 based on at least one of the angle 51 defined by the optical axis 22 of the X-rays and the longitudinal direction (X direction) of the table 1 or the angle 53 defined by the optical axis 22 of the X-rays and the short-side direction (Y direction) of the table 1 and the amount of relative movement (Vectorn [pixel]) of the table 1, and splicing the plurality of X-ray images 40 in each of the aforementioned first and second embodiments, the present invention is not limited to this. For example, the image processor 17 may alternatively be configured to perform processing of varying the magnifications of the plurality of X-ray images 40 based on the angle 51 defined by the optical axis 22 of the X-rays and the longitudinal direction (X direction) of the table 1, the angle 53 defined by the optical axis 22 of the X-rays and the short-side direction (Y direction) of the table 1, and the amount of relative movement (Vectorn [pixel]) of the table 1, and splicing the plurality of X-ray images 40.

While the image processor 17 is configured to perform the processing of varying the magnifications of the plurality of X-ray images 40 based on the amount of relative movement (Vectorn [pixel]) of the table 1 and splicing the plurality of X-ray images 40 when imaging is performed while the table 1 is moved in the longitudinal direction (X direction) of the table 1 in a state in which the optical axis 22 of the X-rays is inclined with respect to the longitudinal direction (X direction) of the table 1, and when imaging is performed while the table 1 is moved in the short-side direction (Y direction) of the table 1 in a state in which the optical axis 22 of the X-rays is inclined with respect to the short-side direction (Y direction) of the table 1 in each of the aforementioned first and second embodiments, the present invention is not limited to this. For example, the image processor 17 may alternatively be configured to perform processing of varying the magnifications of the plurality of X-ray images 40 based on the amount of relative movement (Vectorn [pixel]) of the table 1 and splicing the plurality of X-ray images 40 when imaging is performed while the table 1 is moved in the longitudinal direction (X direction) of the table 1 in a state in which the optical axis 22 of the X-rays is inclined with respect to the longitudinal direction (X direction) of the table 1, or when imaging is performed while the table 1 is moved in the short-side direction (Y direction) of the table 1 in a state in which the optical axis 22 of the X-rays is inclined with respect to the short-side direction (Y direction) of the table 1.

While the image processor 17 is configured to vary the magnifications of the plurality of X-ray images 40 such that the distance 70 between the imaging plane 44 parallel to the detection surface of the X-ray detector 10 and the height position of the region of interest 31 of the subject 30 is the same between the X-ray images 40 in each of the aforementioned first and second embodiments, the present invention is not limited to this. The image processor 17 may alternatively be configured in any manner as long as the same can appropriately splice the plurality of X-ray images 40.

While the image processor 17 is configured to generate the long image 41 while varying the magnifications of the plurality of X-ray images 40 based on a variation in the distance 70 between the imaging plane 44 and the height position of the region of interest 31 of the subject 30 in each of the aforementioned first and second embodiments, the present invention is not limited to this. The image processor 17 may alternatively be configured in any manner as long as the same can appropriately splice the plurality of X-ray images 40.

While the image processor 17 is configured to acquire the distance 70 between the imaging plane 44 and the height position of the region of interest 31 of the subject 30 based on the moving distance 71 of the table 1 at each imaging position 21 and the rotation angle 52 of the imager 2 in each of the aforementioned first and second embodiments, the present invention is not limited to this. The image processor 17 may alternatively be configured in any manner as long as the same can acquire the distance 70 between the imaging plane 44 and the height position of the region of interest 31 of the subject 30.

While the controller 5 includes the image information acquirer 14, the rotation angle acquirer 15, the position information acquirer 16, and the image processor 17 in each of the aforementioned first and second embodiments, the present invention is not limited to this. In the present invention, the image information acquirer 14, the rotation angle acquirer 15, the position information acquirer 16, and the image processor 17 may alternatively be provided separately from the controller 5.

While as the position information of the table 1 acquired by the position information acquirer 16, the coordinate information (X, Y, and Z) is used in each of the aforementioned first and second embodiments, the present invention is not limited to this. In the present invention, the position information of the table 1 is not limited to an orthogonal coordinate system such as the coordinate information (X, Y, and Z), but another coordinate system such as a polar coordinate system may alternatively be used.

While imaging is performed while the table 1 is moved either in a state in which the optical axis 22 of the X-rays is inclined with respect to the longitudinal direction (X direction) of the table 1 or in a state in which the optical axis 22 of the X-rays is inclined with respect to the short-side direction (Y direction) of the table 1 in each of the aforementioned first and second embodiments, the present invention is not limited to this. For example, imaging may alternatively be performed while the table 1 is relatively moved both in a state in which the optical axis 22 of the X-rays is inclined with respect to the longitudinal direction (X direction) of the table 1 and in a state in which the optical axis 22 of the X-rays is inclined with respect to the short-side direction (Y direction) of the table 1. In this case, the magnification varies between the X-ray images 40 regardless of whether the table 1 moves in the longitudinal direction of the table 1 or in the short-side direction of the table 1, and thus it is preferable to apply the present invention.

While the lower limb 32 of the subject 30 is radiographed in each of the aforementioned first and second embodiments, the present invention is not limited to this. In the present invention, a portion other than the lower limb 32 such as the arm or the trunk of the subject 30 may alternatively be radiographed. Furthermore, in the present invention, the X-ray imaging apparatus may alternatively be configured to image a subject of an animal other than the human body.

While the control processing operations of the controller 5 are described using a flowchart in a flow-driven manner in which the processing operations are performed in order along a processing flow for the convenience of illustration in each of the aforementioned first and second embodiments, the present invention is not limited to this. In the present invention, the control processing operations of the controller 5 may alternatively be performed in an event-driven manner in which the processing operations are performed on an event basis. In this case, the control processing operations may be performed in a complete event-driven manner or in a combination of an event-driven manner and a flow-driven manner.

What is claimed is:

1. An X-ray imaging apparatus comprising:
    a table on which a subject is placed;
    an imager including an X-ray irradiator configured to irradiate the subject with X-rays and an X-ray detector configured to detect the X-rays radiated from the X-ray irradiator and transmitted through the subject, the imager being configured to capture a plurality of X-ray images;
    a rotating mechanism configured to rotate the imager;
    a moving mechanism configured to move so as to change a relative position of the table to the imager; and
    an image processor configured to generate a long image, which is longer than each of the plurality of X-ray images, by performing processing of varying magnifications of the plurality of X-ray images based on both of an amount of relative movement of the table and the imager and an inclined angle between the table and the imager, and splicing the plurality of X-ray images when imaging is performed at a plurality of imaging positions while the table and the imager are moved relative to each other in at least one of a short-side direction or a longitudinal direction of the table in a state in which the imager is rotated such that an optical axis of the X-rays radiated from the X-ray irradiator is inclined with respect to the table.

2. The X-ray imaging apparatus according to claim 1, wherein the image processor is configured to perform processing of varying the magnifications of the plurality of X-ray images based on at least one of an angle defined by the optical axis of the X-rays radiated from the X-ray irradiator and the longitudinal direction of the table or an angle defined by the optical axis of the X-rays radiated from the X-ray irradiator and the short-side direction of the table, both of which are formed when the optical axis of the X-rays radiated from the X-ray irradiator is inclined with respect to the table, and the amount of relative movement of the table and the imager, and splicing the plurality of X-ray images.

3. The X-ray imaging apparatus according to claim 1, wherein the image processor is configured to perform processing of varying the magnifications of the plurality of X-ray images based on an amount of relative movement of the table and splicing the plurality of X-ray images when imaging is performed while the table is moved in the longitudinal direction of the table in a state in which the optical axis of the X-rays radiated from the X-ray irradiator is inclined with respect to the longitudinal direction of the table, and when imaging is performed while the table is moved in the short-side direction of the table in a state in which the optical axis of the X-rays radiated from the X-ray irradiator is inclined with respect to the short-side direction of the table.

4. The X-ray imaging apparatus according to claim 1, wherein the image processor is configured to vary the magnifications of the plurality of X-ray images such that a distance between an imaging plane parallel to a detection surface of the X-ray detector and a height position of a region of interest of the subject is the same between the plurality of X-ray images.

5. The X-ray imaging apparatus according to claim 4, wherein the image processor is configured to acquire a magnification for each of the plurality of X-ray images based on the distance between the imaging plane and the height position of the region of interest of the subject that occurs due to imaging with the imager rotated to be inclined with respect to the table, and to generate the long image while varying the magnifications of the plurality of X-ray images based on a variation in the distance between the imaging plane and the height position of the region of interest of the subject that occurs due to the relative movement of the table and the imager in at least one of the short-side direction or the longitudinal direction of the table in a state in which the imager is rotated to be inclined with respect to the table.

6. The X-ray imaging apparatus according to claim 4, further comprising:
    a rotation angle acquirer configured to acquire a rotation angle of the imager; and a position information acquirer configured to acquire position information of the table;

wherein the image processor is configured to acquire the distance between the imaging plane and the height position of the region of interest of the subject based on a moving distance of the table at each of the plurality of imaging positions and the rotation angle of the imager.

7. The X-ray imaging apparatus according to claim 4, wherein:

the height position of the region of interest of the subject is settable; and the image processor is configured to acquire the magnification for each of the plurality of X-ray images based on the distance between the imaging plane and the height position of the region of interest of the subject that has been set.

8. The X-ray imaging apparatus according to claim 1, wherein;

the imager includes a first imager and a second imager configured to capture the plurality of X-ray images in a state in which the second imager is inclined at an angle different from that of the first imager with respect to the subject;

the rotating mechanism includes a first rotating mechanism configured to rotate the first imager, and a second rotating mechanism configured to rotate the second imager; and the image processor is configured to generate the long image by performing processing of varying the magnifications of the plurality of X-ray images captured by the first imager and splicing the plurality of X-ray images, and to generate the long image by performing processing of varying the magnifications of the plurality of X-ray images captured by the second imager and splicing the plurality of X-ray images.

9. The X-ray imaging apparatus according to claim 1, wherein the plurality of X-ray images and the long image include images obtained by imaging a lower limb of the subject.

* * * * *